(12) United States Patent
Yamada et al.

(10) Patent No.: US 11,291,439 B2
(45) Date of Patent: Apr. 5, 2022

(54) ANVIL FOR MEDICAL STAPLER

(71) Applicants: Atsuhiro Yamada, Tokyo (JP); Toshiharu Kamei, Tochigi (JP)

(72) Inventors: Atsuhiro Yamada, Tokyo (JP); Toshiharu Kamei, Tochigi (JP)

(73) Assignee: MANI, INC., Tochigi (JP)

( * ) Notice: Subject to any disclaimer, the term of this patent is extended or adjusted under 35 U.S.C. 154(b) by 0 days.

(21) Appl. No.: 15/862,215

(22) Filed: Jan. 4, 2018

(65) Prior Publication Data
US 2018/0177504 A1    Jun. 28, 2018

Related U.S. Application Data

(62) Division of application No. 14/420,477, filed as application No. PCT/JP2013/071237 on Aug. 6, 2013, now abandoned.

(30) Foreign Application Priority Data

Aug. 8, 2012    (JP) ................................. 2012-175811

(51) Int. Cl.
   *A61B 17/068*    (2006.01)
   *A61B 17/00*    (2006.01)
(52) U.S. Cl.
   CPC ........ *A61B 17/068* (2013.01); *A61B 17/0684* (2013.01); *A61B 2017/00526* (2013.01)
(58) Field of Classification Search
   CPC .............. A61B 17/068; A61B 17/0684; A61B 2017/00526; B21J 5/02–025; B21J 5/12; B21J 13/02
   See application file for complete search history.

(56) References Cited

U.S. PATENT DOCUMENTS 3,584,498 A * 6/1971 Beche ........................ B21J 7/36
                                                              72/453.18
3,638,847 A * 2/1972 Noiles .................. A61B 17/105
                                                              227/120
(Continued)

FOREIGN PATENT DOCUMENTS

AU         3290202        4/2002
AU       2008231109       3/2008
(Continued)

OTHER PUBLICATIONS

International Search Report of PCT/JP2013/071237; dated Sep. 10, 2013.
(Continued)

*Primary Examiner* — Robert F Long
*Assistant Examiner* — Eduardo R Ferrero
(74) *Attorney, Agent, or Firm* — Shlesinger, Arkwright & Garvey, LLP

(57) ABSTRACT

[Problem] To rationalize production steps for a medical stapler.
[Solution] An anvil (A): that forms a medical staple (3) supported in conjunction with a ram (5) in a medical stapler; sutures biological tissue; has dimensions corresponding to the formed peak section in the staple (3) after forming; and has a support section (11) that supports the crown (3b) of the staple (3), and a chamfered corner section (12) formed along both end sections in a direction along the crown (3b) of the staple (3) in the support section (11), which comes in contact with the crown (3b) when the supported staple (3) is formed and regulates a curved section thereof. The chamfered corner section (12) is cured by plastic working and formed.

3 Claims, 5 Drawing Sheets

(56) References Cited

U.S. PATENT DOCUMENTS

| | | | |
|---|---|---|---|
| 3,643,851 A * | 2/1972 | Green | A61B 17/0684 227/120 |
| 3,650,453 A * | 3/1972 | Smith, Jr. | A61B 17/0684 227/136 |
| 3,717,294 A * | 2/1973 | Green | A61B 17/0684 227/19 |
| 3,815,476 A * | 6/1974 | Green | A61B 17/0684 227/130 |
| 3,837,209 A * | 9/1974 | Guse | B21J 7/14 72/402 |
| 4,014,140 A * | 3/1977 | Aoki | B24B 9/00 451/282 |
| 4,041,766 A * | 8/1977 | Johnson | B21F 45/00 72/402 |
| 4,103,407 A * | 8/1978 | Elizalde | B21J 5/12 29/890.12 |
| 4,317,451 A * | 3/1982 | Gerwin | A61B 17/0644 227/19 |
| 4,391,401 A * | 7/1983 | Moshofsky | A61B 17/0684 227/19 |
| 4,519,532 A | 5/1985 | Foslien | |
| 4,523,707 A * | 6/1985 | Blake, III | A61B 17/0684 227/19 |
| 4,526,174 A * | 7/1985 | Froehlich | A61B 17/0684 206/438 |
| 4,606,111 A * | 8/1986 | Okazaki | B21D 53/36 29/463 |
| 4,645,111 A * | 2/1987 | Larrabee | A61B 17/0684 227/120 |
| 4,653,162 A * | 3/1987 | Ferguson | B21K 1/20 269/156 |
| 4,669,647 A * | 6/1987 | Storace | A61B 17/0684 227/155 |
| 4,747,531 A | 5/1988 | Brinkerhoff | |
| 4,789,090 A * | 12/1988 | Blake, III | A61B 17/0684 227/155 |
| 4,848,190 A * | 7/1989 | Doslik | B21J 7/32 76/4 |
| 4,887,756 A | 12/1989 | Puchy | |
| 4,991,763 A * | 2/1991 | Storace | A61B 17/0684 227/119 |
| 5,114,065 A | 5/1992 | Storace | |
| 5,161,725 A * | 11/1992 | Murray | A61B 17/0684 227/121 |
| 5,170,926 A | 12/1992 | Ruckdeschel | |
| 5,174,487 A * | 12/1992 | Rothfuss | A61B 17/0684 227/176.1 |
| 5,289,963 A | 3/1994 | McGarry | |
| 5,356,064 A * | 10/1994 | Green | A61B 17/0684 227/177.1 |
| 5,389,098 A * | 2/1995 | Tsuruta | A61B 17/00234 606/41 |
| 5,497,933 A * | 3/1996 | DeFonzo | A61B 17/0684 227/175.1 |
| 5,560,532 A * | 10/1996 | DeFonzo | A61B 17/0644 227/175.1 |
| 5,651,491 A * | 7/1997 | Heaton | A61B 17/07207 227/175.1 |
| 5,697,738 A * | 12/1997 | Stone | B21K 5/02 408/225 |
| 5,842,267 A * | 12/1998 | Biederman | B21J 9/06 29/558 |
| 5,908,149 A | 6/1999 | Welch | |
| 5,911,352 A * | 6/1999 | Racenet | A61B 17/07207 227/175.1 |
| 6,056,183 A | 5/2000 | Tanabe | |
| 6,228,098 B1 | 5/2001 | Kayan | |
| 6,427,326 B1 * | 8/2002 | Soga | B21J 5/02 29/888.09 |
| 6,953,138 B1 * | 10/2005 | Dworak | B21D 13/02 227/175.1 |
| 7,059,509 B2 | 6/2006 | Brown | |
| 7,311,236 B2 | 12/2007 | Smith | |
| 7,510,106 B2 | 3/2009 | Manabe | |
| 7,942,304 B2 | 5/2011 | Taylor | |
| 9,085,088 B2 | 7/2015 | Yagi | |
| 2002/0047035 A1 | 4/2002 | Coleman | |
| 2002/0101041 A1 * | 8/2002 | Kameyama | H01R 13/521 277/628 |
| 2004/0232201 A1 | 11/2004 | Wenchell | |
| 2005/0004582 A1 | 1/2005 | Edoga | |
| 2005/0082336 A1 | 4/2005 | Ivanko | |
| 2005/0085830 A1 * | 4/2005 | Lehman | A61B 17/1285 606/143 |
| 2005/0145671 A1 * | 7/2005 | Viola | A61B 17/0686 227/175.1 |
| 2006/0191974 A1 * | 8/2006 | Matsutani | A61B 17/0684 227/175.1 |
| 2006/0243774 A1 | 11/2006 | Matsutani | |
| 2007/0057014 A1 | 3/2007 | Whitman | |
| 2007/0107484 A1 * | 5/2007 | Otaki | B21J 5/08 72/355.6 |
| 2007/0131732 A1 | 6/2007 | Holsten | |
| 2008/0078804 A1 | 4/2008 | Shelton | |
| 2008/0082126 A1 | 4/2008 | Murray | |
| 2008/0300632 A1 * | 12/2008 | Butler | A61B 17/7059 606/246 |
| 2010/0072251 A1 | 3/2010 | Baxter, III | |
| 2010/0187285 A1 * | 7/2010 | Harris | A61B 17/064 227/179.1 |
| 2011/0029015 A1 * | 2/2011 | Kamei | A61B 17/0684 606/219 |
| 2011/0144676 A1 * | 6/2011 | Yamaguchi | A61B 17/3211 606/167 |
| 2011/0226837 A1 | 9/2011 | Baxter, III | |
| 2011/0315741 A1 | 12/2011 | Nelson | |
| 2012/0175401 A1 | 7/2012 | Bachman | |
| 2012/0193398 A1 | 8/2012 | Williams | |
| 2012/0239010 A1 | 9/2012 | Shelton, IV | |
| 2012/0325890 A1 * | 12/2012 | Matsutani | A61B 17/0684 227/176.1 |
| 2012/0330329 A1 * | 12/2012 | Harris | A61B 17/0644 606/153 |
| 2013/0001271 A1 * | 1/2013 | Kamei | A61B 17/0684 227/176.1 |
| 2014/0013574 A1 * | 1/2014 | Giasolli | A61B 90/39 29/505 |
| 2015/0182218 A1 * | 7/2015 | Yamada | A61B 17/0684 227/175.1 |

FOREIGN PATENT DOCUMENTS

| | | |
|---|---|---|
| JP | 63255048 | 10/1988 |
| JP | 2006305136 | 11/2006 |
| JP | 2011206520 | 10/2011 |
| WO | WO2014024875 | 2/2014 |

OTHER PUBLICATIONS

English language Abstract of JP2006/3305136; Mani KK.
Joseph R. Davis, ASM Specialty Handbook, 1994, p. 7.

* cited by examiner

ANVIL FOR MEDICAL STAPLER

CROSS-REFERENCE TO RELATED APPLICATIONS

This application is a divisional of application Ser. No. 14/420,477, filed Feb. 9, 2015, which is a National Stage of International Application PCT/JP2013/071237, filed Aug. 6, 2013, both of which are incorporated herein by reference.

TECHNICAL FIELD

The present invention relates to a structure of anvils for medical staplers used in suturing body tissue.

BACKGROUND ART

In surgical operations, incised body tissue is sutured with a medical stapler. The medical stapler sutures an affected area of a patient in the processes of moving a ram toward an anvil while the anvil supporting a crown (middle part) of a medical staple, and then shaping the medical staple into a rectangle with a pair of leg parts formed at both widthwise ends of the ram. The medical staple for suturing an affected area of a patient is made from a metal rod and formed in a square U-shape having a straight crown, and a pair of legs formed at both ends of the crown and bent substantially at right angle relative to the crown.

The anvil for the medical stapler is configured such that the anvil supports the crown of a medical staple that has been fed so that the staple is finely shaped, and also that the anvil enables a shaped medical staple to leave smoothly. As such an anvil, there is one that accommodates a plurality of medical staples as placed therein and is integral with the magazine for successively feeding a staple to the anvil. In this structure, the anvil protrudes in cantilever fashion from the distal end of the magazine (refer to Patent Literature 1, for example).

There is also a medical stapler in which a housing accommodates a plate-like member provided with an anvil such that the member is movable toward the suturing site and also accommodates a ram constituted by a plate-like member such that the ram is movable toward the anvil and the suturing site. In the medical stapler configured as described above, the anvil is opposed to the accommodating part for receiving a medical staple, then in this state, only the ram is moved to hold the medical staple between itself and the anvil, and the anvil and the ram are simultaneously brought closer to the site to be sutured and the ram is moved toward the anvil, thereby shaping the medical staple. The anvil is formed in cantilever fashion also in this structure.

The medical staple that has sutured an affected area of a patient as it is shaped into a rectangle begins to return to its initial configuration due to spring back. Spring back would unfavorably interfere with the intention to keep the sutured site from opening. Therefore, in an anvil of the medical stapler, corners at both widthwise (the length direction of a medical staple) ends, which serve as fulcrum for shaping a medical staple, are generally formed at an acute angle or substantially at right angle (refer to Patent Literature 2, for example) in order to shape the bending portions of a medical staple substantially at right angle and to minimize spring back.

The anvil for the medical stapler configured as described above supports a portion at the center of the crown of a medical staple and with a length substantially twice the legs. Accordingly, the legs at both ends of the medical staple protrude in cantilever fashion from the anvil, and when the leg parts of the ram abut the crown and start shaping the staple, the crown curves with a fulcrum located at the both widthwise (the length direction of a medical staple) ends. Thus, when shaping a medical staple, the shaping force is concentrated on both widthwise ends of the anvil.

The concentration of the medical staple shaping force results in recesses at both ends of the anvil, which grow with the number of shaping times. As a result, a medical staple will not be finely shaped or a shaped medical staple will not leave smoothly.

To solve the above problems, in a recent medical stapler, the entire anvil is hardened. More precisely, the anvil is press-molded using a material that is expected to be hardened by quenching and precipitation, and then subjected to heat treatment for hardening.

On the other hand, in order for a shaped medical staple to smoothly leave the anvil, the anvil is generally inclined at a predetermined angle relative to the holding part that holds medical staples as they are aligned.

CITATION LIST

Patent Literature

Patent Literature 1: JP 2006-305136 A
Patent Literature 2: JP 2011-206520 A

SUMMARY OF INVENTION

Technical Problem

However, when hardened by heat treatment, an anvil is slightly deformed (bent). This makes unstable the inclination angle of the anvil relative to the holding part that is set in order for medical staples to leave smoothly, possibly preventing shaped medical staples from leaving smoothly.

The present invention aims to provide an anvil for a medical stapler which, even after shaping a substantial number of staples, keeps shaping a staple finely and also enables a shaped medical staple to leave smoothly.

Solution to Problem

To solve the above problems, according to the present invention, an anvil for a medical stapler suturing body tissue by shaping, in cooperation with a ram of the medical stapler, a medical staple supported by the anvil, includes a supporting part with a dimension corresponding to a dimension of a shaped top part in the shaped medical staple, the supporting part supporting a middle part of the medical staple and a corner formed on both ends in a direction along the middle part of the medical staple on the supporting part, the corner contacting the middle part of the medical staple in shaping of the supported medical staple and defining a portion to be bent, wherein the corner is formed as a chamfered corner hardened by plastic working.

In the anvil for a medical stapler, the supporting part is preferably formed in cantilever fashion with a protruding dimension larger than a thickness of the middle part of the medical staple, and also the chamfered corner hardened by plastic working preferably extends from a shaping position in the cantilevered supporting part at which the medical staple is shaped to a free end of the supporting part.

Advantageous Effects of Invention

In the anvil for a medical stapler (referred to simply as "stapler" hereinafter) according to the present invention, a corner contacting a middle part (referred to as "crown" hereinafter) of a supported medical staple (referred to as "staple" hereinafter) in shaping of the staple for defining a portion to be bent is formed as a chamfered corner hardened by plastic working (cold forging). This eliminates the need for a heat treatment process in manufacturing the anvil, thereby preventing the anvil from being deformed by the heat treatment. Therefore, an inclination angle of the anvil relative to a holding part can be maintained constant, enabling the staple to leave smoothly.

In manufacturing the anvil, only corners of a material corresponding to the anvil have to undergo plastic working. Therefore, compared with the case where an entire portion corresponding to the anvil undergoes press working, the anvil can be manufactured more simply without the need for considering a change in width dimension.

In particular, even when a force concentrates on the corners in shaping a staple, no recess is formed on the corners. Therefore, the stapler can keep shaping a staple finely, and can stably shape a staple even after shaping a substantial number of staples.

The supporting part of the anvil is formed in cantilever fashion with a protruding dimension larger than a thickness of the middle part of the medical staple, and the chamfered corner hardened by plastic working extends from a shaping position in the cantilevered supporting part to a free end, thereby preventing a level difference from occurring on the surface of the anvil. Therefore, a shaped staple will not be prevented from leaving smoothly.

In particular, because the chamfered corner that is hardened is formed on the anvil protruding in cantilever fashion, bending strength is improved. Therefore, even when the staple is shaped on the distal end, a free end, the anvil can sufficiently counter the force.

DESCRIPTION OF EMBODIMENT

Figure 1:
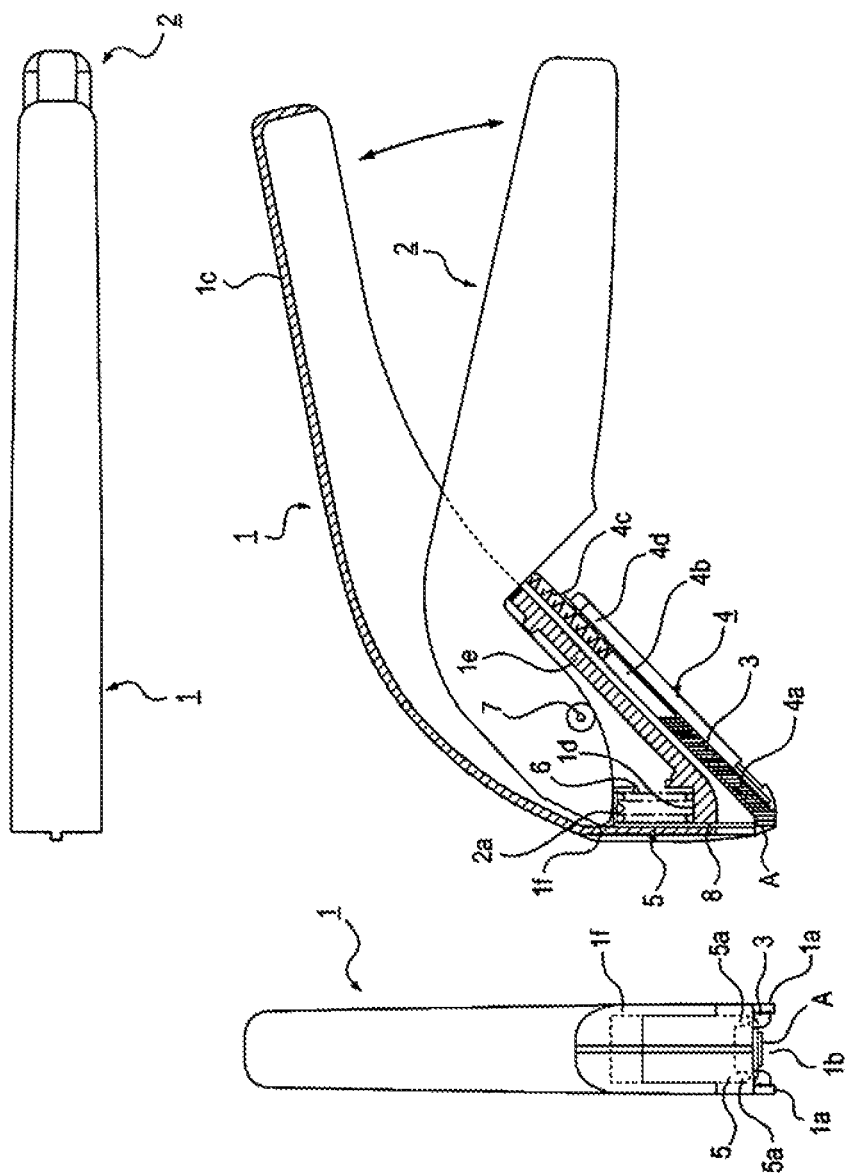
FIGS. 1A, 1B and 1C are three orthographic views explaining the configuration of a stapler.
Figure 2:
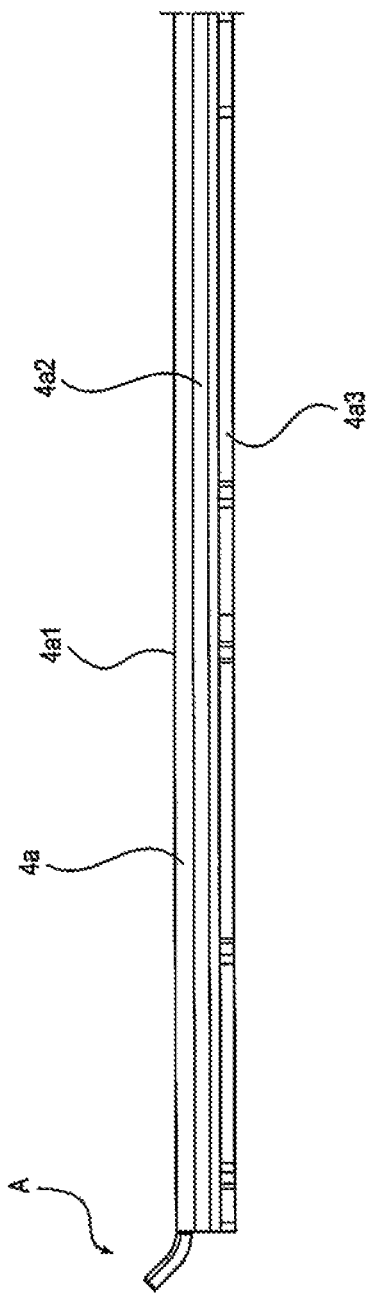
FIG. 2 is a view explaining the anvil integral with the holding part accommodating a staple.
Figure 3:
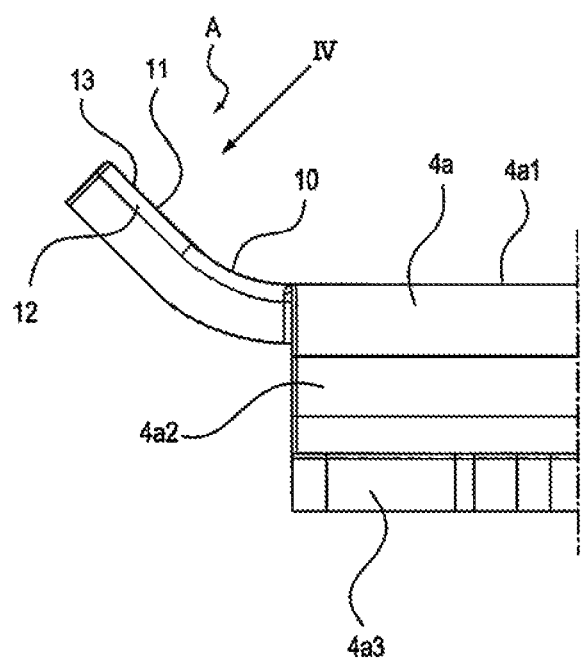
FIG. 3 is an enlarged side view of the anvil, the view explaining the configuration thereof.

The configuration of the anvil for a stapler according to the present invention will be explained hereinafter. The anvil according to the present invention supports a staple formed in a square U-shape including a crown and a pair of legs and shapes the supported staple into a square O-shape in cooperation with a ram. In particular, both corners of the anvil in the direction along the length of the staple (width direction of the anvil) when the staple is supported are formed as chamfered corners which are hardened by plastic working, and thus the anvil is improved in strength to stably shaping a staple.

The anvil of the present invention has functions of receiving and supporting a staple, and of, even when a force imparted from the ram to a staple in shaping concentrates on the chamfered corners, supporting the force. Also, after finishing shaping a staple, the anvil enables the staple to leave smoothly. Therefore, the configuration and the properties of the anvil are not limited as long as the anvil can exercise the functions.

For example, the anvil may be formed integrally with a magazine accommodating a plurality of staples for successively receiving the staples from the magazine. Alternatively, the anvil may be formed separately from the magazine and receive a staple by opposing the magazine in association with the operation of suturing an affected area of a patient.

The anvil may have any properties as long as it is hardened by plastic working. However, for the stapler, because rusting in the distribution stage is not desirable, preferably used is austenitic stainless steel, which will not rust. The austenitic stainless steel is not expected to be hardened by heat treatment, but can be hardened by cold working.

If subjected to rust prevention treatment in the distribution stage, martensitic stainless steel, precipitation hardening type stainless steel, or steel are expected to be hardened by cold plastic working. Accordingly, the anvil may be made of martensitic stainless steel, precipitation hardening type stainless steel, or steel.

As the plastic working for hardening the corners of the anvil, is performed the cold forging in which the corners are crushed for increasing strength, not the forming processing including punching of a material by a press and bending, thereby achieving work hardening. That is, the material is subjected to plastic deformation as it is reduced in cross-sectional area, thereby achieving work hardening.

Thus, as to the plastic working for the corners of the anvil, it is only required to harden the corners so that they can sufficiently counter the force acting thereon when a staple supported by the anvil is shaped, and the shape of the chamfered corners formed is not limited as long as the shape does not have negative effect on the staple shaping work or does not cause any trouble to a shaped staple. Accordingly, the shape of the chamfered corners may be selected from round chamfering, chamfering, and chamfering into polygonal shape.

The chamfered corners of the anvil need to be hardened enough to counter the force acting thereon when a staple is shaped. Thus, the reduction ratio of the corners of the anvil is defined appropriately in consideration of material conditions such as properties and thickness of the material for the anvil and staple conditions such as properties, surface hardness, and thickness of a staple. Therefore, chamfer dimensions of the chamfered corners formed on the anvil is not limited.

The present inventors have found out from experiences a hardness of a chamfered corner that enables fine shaping of plural staples and prevents recesses even after shaping all staples accommodated in the stapler, and the reduction ratio that exhibits the hardness by plastic working.

More specifically, anvils having chamfered corners with different hardnesses were prepared for observing the shaping performance of a staple and the development of a recess associated with shaping of pluralities of staples. As a result, it was found out that the lowest hardness that enables fine shaping of staples and prevents deformation even after shaping pluralities of staples (as many staples as the medical stapler may hold) was Hv360.

It was observed that an anvil having chamfered corners of a hardness higher than the above enables stable shaping of staples with stable shapes, and smooth discharge of the shaped staples. In particular, for more stability the hardness is preferably Hv420 or more and about Hv590 at most.

Figures 4A, 4B:
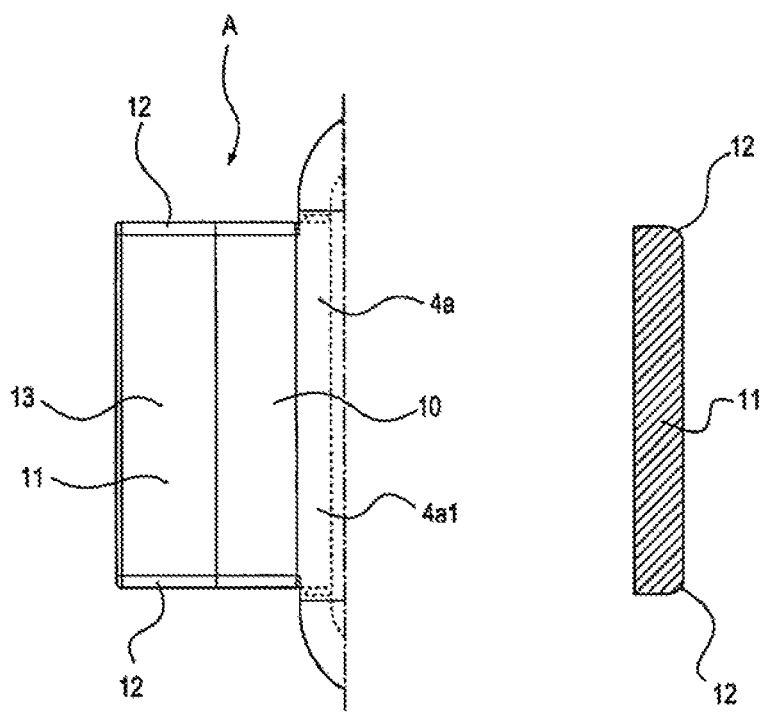
FIGS. 4A and 4B are enlarged plan views of the anvil taken along an arrow IV in FIG. 3, the views explaining the configuration thereof.

Referring to FIG. 4(b), the reduction ratio will be explained that allows the chamfered corners to exhibit the above hardness, when the anvil is made of SUS301, austenitic stainless steel. In a cross section of a supporting part 11 of an anvil A, when a perpendicular is drawn from a point at which the cross section begins to decrease by chamfering (inner starting point of a chamfered corner 12) to the bottom surface (back surface) of the supporting part 11, a cross sectional area from the perpendicular to the side edge of the supporting part 11 including the outer edge of a nearer chamfered corner 12 is subtracted from the same area before plastic working (a cross sectional area from the perpendicular to the side edge of the supporting part 11 including the corner of the nearer chamfered corner 12, hereinafter referred to as corner cross section), thereby obtaining a reduced cross sectional area. The reduction ratio was expressed by the ratio of the reduced cross sectional area to the corner cross section.

That is, reduction ratio=reduced cross sectional area/corner cross section×100(%).

Many samples were prepared which were varied in the reduction ratio in plastic working of the chamfered corner. Hardnesses of the samples were then measured. As a result, the reduction ratio achieving a hardness of Hv360 was 7%. Chamfered corners with reduction ratio of more than 7% have a hardness of more than Hv360. However, increase in hardness without limitation unfavorably causes a crack on the supporting part. Accordingly, the hardness is about Hv590 at most.

The configuration of a stapler using an anvil according to the present invention will be explained referring to the figures. The stapler in FIG. 1 includes a housing 1, a lever 2 rotatably attached to the housing 1 and having a drive part 2a at one end, an accommodating part 4 placed at the lower end of the housing 1 and accommodating a plurality of staples 3, an anvil A formed continuously on a holding part 4a constituting the accommodating part 4 and unmovable relative to the housing 1, a ram 5 formed movable toward the anvil A and shaping a staple 3 supported by the anvil A, and a biasing member 6 biasing the ram 5 toward the drive part 2a of the lever 2.

The housing 1 and the lever 2 are made of synthetic resin (ABS resin, in the embodiment), and shaped in consideration of grippability and operability. At the lower part of the front face of the housing 1 is formed a pair of abutment pieces 1a abutting on both end parts of the unshaped staple 3 supported by the anvil A for preventing the staple 3 from leaving the stapler. Between the abutment pieces 1a is formed an opening 1b through which the shaped staple 3 passes when it leaves the anvil A.

A pivot 7 is placed in a predetermine position of the housing 1 and the lever 2 is rotatably attached to the pivot 7. A gripping part 1c of the housing 1 has a square U-shaped cross section. With this shape, when the lever 2 is operated to rotate, the housing 1 can accommodate the lever 2. A flange 1e having a seat 1d for the biasing member 6 is formed at a position of the housing 1 corresponding to the accommodating part 4.

A guiding part 8 guiding the ram 5 is formed inside a front wall 1f of the housing 1 and between the front wall 1f and the flange 1e. The guiding part 8 is formed by a slot slightly wider than the board thickness of the ram 5 and guides the ram 5 to move toward or away from the anvil A by fitting both widthwise ends of the ram 5 into the slot.

Figure 5A:
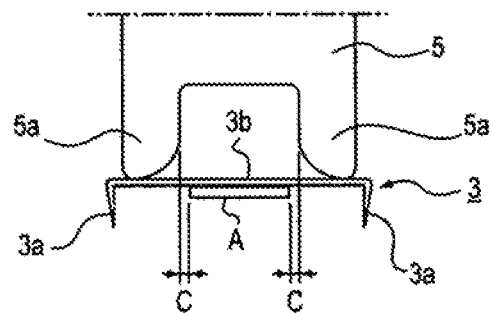
FIGS. 5A, 5B and 5C are views explaining a shaping process of a staple.
Figure 5B:
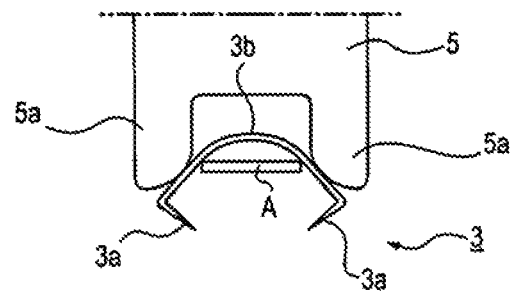
Figure 5C:
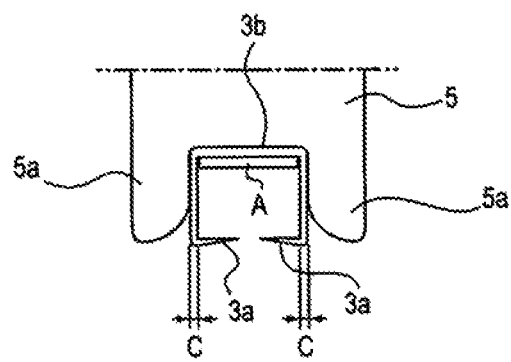

The staple 3 is a rod of stainless steel formed into a square U-shape. As shown in FIGS. 5(a) to 5(c), the staple 3 has at the both ends a pair of legs 3a with a sharp point for reducing resistance acting when piercing body tissue and has at the middle portion a crown 3b, a middle part. The crown 3b is a portion to be bent when suturing body tissue.

A predetermined number of staples 3 are accommodated in the accommodating part 4 as they are arranged. The accommodating part 4 includes a holding part 4a continuing to the anvil A at the front end position and holding the staples 3 as they are arranged, an abutting member 4b abutting the staple 3 accommodated in the holding part 9a, a biasing member 4c biasing the staples 3 toward the abutment pieces 1a of the housing via the abutting member 4b, and a casing 4d accommodating the holding part 4a, the abutting member 4b, and the biasing member 4c.

The holding part 4a has functions of holding a predetermined number of staples 3 and of, after a foremost staple 3 is shaped and leaves the anvil A, guiding staples 3 biased by the biasing member 4c. Especially, the holding part 4a continues to and is integral with the anvil A in order for staples 3 to be smoothly fed to the anvil A.

The holding part 4a is formed into a Ω-shape when viewed from the front for stably holding and also smoothly moving pluralities of staples 3. That is, the top of the holding part 4a is configured as a flat part 4a1 placing thereon and guiding the crowns 3b of the staples 3. At both widthwise (the direction along the length of the crowns 3b) ends of the flat part are formed drooping parts 4a2 each drooping downward. The lower ends of the drooping parts are each bent outward to form leg guiding parts 4a3 guiding legs 3a of the staples 3.

The abutting member 4b is formed to have a shape similar to that of a staple 3, abuts on the rearmost staple 3 arranged in the holding part 4a, and biases staples 3 toward the anvil A by being biased by the biasing member 4c such as a compression spring. The casing 4d is fixed to the housing 1 to prevent the accommodating part 4 and the anvil A from moving relative to the housing 1.

The ram 5 is driven by the lever 2 to move toward the anvil A, during which the ram 5 shapes a staple 3 supported by the anvil A. The upper end part of the ram 5 is bent substantially at right angle. The bent part abuts at the upper surface on the drive part 2a of the lever 2 and at the lower surface on an end of the biasing member 6. A pair of leg parts 5a is formed at both widthwise sides of the lower end of the ram 5.

When a user exerts force on the lever 2 to rotate it counterclockwise as in FIG. 1, the ram 5 is driven in response to the rotation to move toward the anvil A (downward). When the force exerted to the lever 2 is removed, the ram 5 is biased by the biasing member 6 to move away from the anvil A (upward). As the ram 5 moves upward, the lever 2 is biased to rotate clockwise.

The pair of leg parts 5a provided to the ram 5 shapes a staple 3 supported by the anvil A. Each leg part 5a has a shaping area on the surface thereof facing the anvil A. In particular, a clearance C between the shaping area of the leg part 5a and an end of the anvil A has a dimension equal to the thickness of a staple 3 plus a clearance dimension required in shaping the staple 3.

The shaped configuration of the staple 3 has a square shape where the points of the pair of legs 3a oppose to each other with a slight distance therebetween and bending portions of the crown 3b are substantially at right angle. The length of the legs 3a of the staple 3 is about half of the width of the anvil A. The reason why the bending portions of the crown 3b is "substantially" at right angle is that the shaped staple 3 is not an exact square due to spring back occurring simultaneously with the release of the restraint of the ram 5.

Here, the shaping sequence of the staple 3 is simply explained referring to FIGS. 5(a) to 5(c). In FIG. 5(a), after the ram 5 moves down, the leg parts 5a abut on the crown 3b of a staple 3 supported by the anvil A. In this state, no force acts on the staple 3, and thus the staple 3 retains the initial configuration.

As shown in FIG. 5(b), when the ram 5 continues moving down, because the lower part of the staple 3 is supported by the anvil A, the leg parts 5a apply bending force to the crown 3b of the staple 3. The applied bending force causes a bend to the crown 3b of the staple 3 with a fulcrum located at the corners of the anvil A. In the course of the process, the legs 3a pierce an affected area of a patient to start suturing.

As shown in FIG. 5(c), a further downward movement of the ram 5 increases the bend of the staple 3 to bend the crown 3b substantially at right angle with a fulcrum located at the corners of the anvil A, and to bring the legs 3a close to each other until the points oppose to each other, thereby shaping the staple 3 into a rectangle. An affected area of a patient is sutured with the shaping of the staple, and the shaped staple 3 leaves the anvil A and also passes through the opening 1b of the housing 1.

An affected area of a patient can be sutured as described above.

The configuration of the anvil A will be explained next referring to FIGS. 2 to 4(b). As described above, the anvil A in the embodiment continues to the holding part 4a of the accommodating part 4 accommodating a plurality of staples 3 and feeding a staple 3 to the anvil A and protrudes in cantilever fashion from the holding part 4a. The anvil A is not formed in the same plane as the upper surface of the holding part 4a, but protrudes as inclined at a predetermined angle relative to the holding part 4a. By thus inclining the anvil A at a predetermined angle relative to the holding part 4a, a staple 3 can smoothly leave the anvil A.

The anvil A includes a connecting part 10 connecting to the holding part 4a, a supporting part 11 supporting the staple 3, and chamfered corners 12 formed at both widthwise ends of the supporting part 11. A position on the free end side of the supporting part 11 and facing the ram 5 when the holding part 4a is mounted on the casing 4d is defined as a shaping position 13.

Accordingly, staples 3 accommodated in the holding part 4a reaches the connecting part 10 and the supporting part 11 continuing from the holding part 4a and constituting the anvil A. Then, both end portions (the legs 3a and the both ends of the crown 3b) of a foremost unshaped staple 3 abut on the abutment pieces 1a of the housing 1, thereby holding the staples.

The connecting part 10 is curved according to the predetermined inclination angle of the supporting part 11 relative to the holding part 4a for the staple 3 to smoothly move from the holding part 4a to the supporting part 11. The angle made by the holding part 4a and the supporting part 11 is not uniquely set, but set in a stapler design stage. Therefore, conditions like a radius or a length of the arc of the connecting part 10 are not limited, but are set appropriately to meet a particular stapler. The connecting part 10 is not always necessary, and in some anvils A, a supporting part 11 is directly connected to a holding part 4a.

The supporting part 11 continues to the curved connecting part 10 and protrudes in straight beam manner. The front end of the supporting part 11, a free end, extends into the opening 1b beyond a foremost staple 3 for reliably supporting the staple 3. The opening 1b is a part through which a staple 3 shaped into a rectangle passes when the staple 3 leaves the anvil A and the housing 1, and is shorter than the length of an unshaped staple 3 (a dimension between the outsides of the pair of legs 3a via the crown 3b).

Therefore, when an affected area of a patient is sutured, the one positioned foremost among pluralities of staples 3 supported by the supporting part 11 is used, and a position on the supporting part 11 corresponding to a position of a foremost staple 3 is defined as a shaping position 13.

As shown in detail in FIGS. 4(a) and 4(b), the chamfered corners 12 are hardened by plastic working (cold forging), and extends from the shaping position 13 to the free end in the supporting part 11 of the anvil A. That is, the chamfered corners 12 only need to extend from a position of a foremost staple 3 supported by the supporting part 11 to the free end when the holding part 4a integral with the anvil A is mounted on the casing 4d. The chamfered corners 12, however, preferably extend along the entire length of the supporting part 11 in consideration of the condition that the holding part 4a and the anvil A are small in dimensions, or conditions of dimensional tolerances set in forming processing, and of dimensional tolerances of the housing 1.

In the present embodiment, the material forming the anvil A and the holding part 4a has the properties of SUS301, austenitic stainless steel, and has a thickness of 0.70 mm. A width dimension set for the supporting part 11 is 5.30 mm.

In manufacturing the anvil A and the holding part 4a as described above, a SUS301 stainless steel plate with a thickness of 0.70 mm is punched to provide a battledore-shape material including a wide portion corresponding to the holding part 4a and a narrow portion corresponding to the anvil A. In the material of this state, roll over occurs along the entire perimeter in association with punch press.

The roll over occurs on the upper and the lower surfaces of the plate, similarly to bending forming. This more or less hardens the perimeter of the material, but not like cold forging, does not cause significant hardening. The roll over can be reduced by setting a clearance of a punch press die to an appropriate dimension.

The holding part 4a including the drooping parts 4a2 and the leg guiding parts 4a3 are formed by folding the wide portion of the material. By the formation of the holding part 4a, a piece constituting the anvil A protrudes in cantilever fashion from the flat part 4a1.

On a portion of the cantilever piece corresponding to the supporting part 11 of the anvil A, both widthwise corners are formed into the chamfered corners 12 by plastic working. The both corners of the supporting part 11 undergoes plastic working as an upper die presses the both corners while a lower die supports the corners from below. Thus, the material undergoes cold forging, where the upper corners of the supporting part 11 are crushed to the shape corresponding to the upper die shape, thereby hardening the both corners.

In the embodiment, the chamfered corners 12 are formed to R0.20 as the punch pressed material undergoes plastic working. Thus formed chamfered corners 12 had a hardness of Hv360. With chamfered corners 12 having the dimension and the hardness, no recess is formed even after shaping all staples 3 accommodated in the holding part 4a, thereby enabling staples 3 to be finely shaped and the shaped staples 3 to leave smoothly.

INDUSTRIAL APPLICABILITY

The anvil of the present invention is effectively utilized for a medical stapler used in suturing incision area in surgical operations.

REFERENCE SIGNS LIST

A Anvil
1 Housing
1a Abutment piece
1b Opening
1c Gripping part
1d Seat
1e Flange
1f Front wall
2 Lever
2a Drive part
3 Staple
3a Leg
3b Crown
4 Accommodating part
4a Holding part
4a1 Flat part
4a2 Drooping part
4a3 Leg guiding part
4b Abutting member
4c Biasing member
4d Casing
5 Ram
5a Leg part
6 Biasing member
7 Pivot
8 Guiding part
10 Connecting part
11 Supporting part
12 Chamfered corner
13 Shaping position

We claim:

1. A method of producing an anvil for a medical stapler suturing body tissue by shaping, in cooperation with a ram of the medical stapler, a medical staple supported by the anvil, the anvil including:
 a supporting part with a dimension corresponding to a dimension of a shaped top part in the shaped medical staple, the supporting part supporting a middle part of the medical staple, the supporting part having a first end in a first direction along the middle part of the medical staple on the supporting part and a second end in a second direction opposite to the first direction;
 a first corner formed on the first end of the supporting part, the first corner contacting the middle part of the medical staple and defining a first portion of the middle part to be bent in shaping the supported medical staple; and
 a second corner formed on the second end of the supporting part, the second corner contacting the middle part of the medical staple and defining a second portion of the middle part to be bent in shaping the supported medical staple,
 the method comprising the step of pressing only the first corner and the second corner so as to respectively form a chamfered corner such that the chamfered corner has a rounded shape in a cross section along the middle part of the medical staple on the supporting part and so as to harden only the first corner and the second corner by cold forging,
 wherein after the step of pressing the first corner and the second corner, the supporting part of the anvil becomes of a single continuous shape without a recessed portion,
 wherein in the step of pressing the first corner and the second corner, a reduction ratio of the first corner and the second corner is determined such that the hardness of the first corner and the second corner is within a predetermined range,
 wherein the predetermined range is Hv360 to Hv590, and
 wherein after the step of pressing the first corner and the second corner, the reduction ratio is equal to or greater than 7%.

2. The method of producing an anvil for a medical stapler according to claim 1,
 further comprising the step of forming the supporting part in cantilever fashion with a protruding dimension larger than a thickness of the middle part of the medical staple,
 wherein the step of pressing only the first corner and the second corner is performed such that the chamfered corners hardened by cold forging extend from a shaping position on the cantilevered supporting part at which the medical staple is shaped to a free end of the supporting part.

3. The method of producing an anvil for a medical stapler according to claim 1,
 wherein the step of pressing only the first corner and the second corner comprises the steps of:
 supporting the supporting part with a lower die from below; and
 pressing only the first corner and the second corner with an upper die.

* * * * *